United States Patent [19]
Zoughi et al.

[11] Patent Number: 5,539,322
[45] Date of Patent: Jul. 23, 1996

[54] CALIBRATED MICROWAVE DIELECTRIC COATING THICKNESS GAUGE

[75] Inventors: Reza Zoughi; Stoyan I. Ganchev, both of Fort Collins, Colo.

[73] Assignee: Wave Metric, Inc., Denver, Colo.

[21] Appl. No.: 309,170

[22] Filed: Sep. 20, 1994

[51] Int. Cl.$^6$ ................................................. G01N 22/00
[52] U.S. Cl. ........................... 324/644; 324/642; 324/645; 427/9
[58] Field of Search ................................. 324/637, 639, 324/642, 644, 645; 427/7, 8, 9

[56] References Cited

U.S. PATENT DOCUMENTS

| | | | |
|---|---|---|---|
| 3,562,642 | 2/1971 | Hochschild | 324/642 |
| 4,492,915 | 1/1985 | Caspers | 324/637 X |
| 5,012,248 | 4/1991 | Munio et al. | 324/644 X |
| 5,057,781 | 10/1991 | Atkins et al. | 324/644 X |
| 5,216,372 | 6/1993 | Zoughi et al. | 324/642 X |

*Primary Examiner*—Kenneth A. Wieder
*Assistant Examiner*—Diep Do
*Attorney, Agent, or Firm*—Richard W. Hanes

[57] ABSTRACT

The present invention relates to a method and related apparatus for the nondestructive determination of n layers of coating of a target having n layers of dielectric coating applied to an electrically conductive base material, comprising; a generator of electromagnetic waves in the microwave frequency range, including a microwave oscillator, a waveguide attached to the oscillator output and having an output aperture, a voltage detecting diode disposed within the waveguide, a flat layer of material adapted to be placed in a position abutting the target and disposed over the aperture of the waveguide and having a thickness t which, together with the waveguide, will provide a fixed distance between the diode and the target, and a display responsive to the output of the detecting diode for indicating the layer characteristics of the dielectric coating on the electrically conductive base material.

7 Claims, 3 Drawing Sheets

CALIBRATED MICROWAVE DIELECTRIC COATING THICKNESS GAUGE

The present invention relates generally to a method for measuring the thickness of a coating, such as paint, and resolving that measured thickness into counted layers of that coating material on a metallic surface. More specifically, the invention relates to a preferred form of electronic microwave transmitter and receiver apparatus to carry out the process.

BACKGROUND

It is often necessary or desirable to nondestructively determine whether a painted metallic surface has been painted more than once or whether there exits between the metal surface and the paint layer another material, such as a body filler. This information is useful, for example, in determining the condition and value of used motor vehicles. Revelation of the presence of several paint layers or body fillers on some portion of a used car body would undoubtedly indicate previous damage and subsequent repair to that portion of the vehicle, although no such history would be revealed by mere visual observation of the outside of the vehicle.

One of the prior methods of determining the thickness of layered targets consisting of a number of dielectric layers involves the use of electromagnetic waves having related frequencies such as a fundamental and its harmonics to establish a multi-harmonic coherence relationship whereby a homodyne phase reference between harmonics can be conserved and information can be extracted from just the received and not the transmitted signals. Such a device is disclosed in U.S. Pat. No. 4,075,555 to James S. Wight, et al. In this arrangement, the necessary hardware to extract the phase is relatively complicated, expensive and does not always result in apparatus which may be handheld or which is portable. Furthermore, the resolution of the measurement is rated in fractions of a centimeter or several millimeters, which is far too low and completely inadequate for the purposes of the present invention. Frequently, devices of this general type, as disclosed in U.S. Pat. No. 5,216,372 to Zoughi et al. use multiple diode detectors in a waveguide separated from each other by very specific distances. Such multiple spaced diodes must be calibrated for the differences in the power-in, voltage-out characteristics which may change during the operation, making the approach limited to stationary devices, as opposed to easily portable ones.

Another device directed to apparatus for measuring properties of materials by sensing signals responsive to both amplitude and phase changes in transmitted or reflected microwave energy is disclosed in U.S. Pat. No. 3,562,642 issued to Richard Hochschild. The teachings of this disclosure are not pertinent to the invention herein described for many reasons, but Hochschild's use of multiple detectors is one distinction.

U.S. Pat. No. 4,818,930 to Flemming, et al. disclosed apparatus for measuring the thickness of a thin layer of a non-metallic material on the surface of another medium, however this device requires the transmission of an incident beam at an angle of incidence greater than 30 degrees and the detection of polarized reflections, neither of which is a part of the invention to be described.

To the knowledge of the inventors there are no other prior art disclosures which would be pertinent to the invention which is the subject of the disclosure made herein.

It is therefore the primary object of the present invention to provide a coatings layer counter for layers of paint (or other dielectric layered materials) applied to metallic or other electrically conductive surfaces which requires only one detector diode and is otherwise simple enough in its design and construction to be hand held and modest enough in its theory of operation that it can successfully determine the layer count with required resolution by measuring the magnitude of only one voltage component of a standing wave of microwave energy.

Another object of the invention is to provide a device of the character described which will be relatively inexpensive and yet reliable and will have good repeatability and sufficient resolution to detect at least one half of a normal paint layer, or better.

A further object of the invention is to provide a microwave transmitting and receiving apparatus which requires no antenna and one which will operate as a near field measuring device, as opposed to a far field device.

Yet another object of the invention is to provide a microwave instrument for measurement using only a fixed diode location which depends for its success only on the magnitude of the standing wave at a specific location in the waveguide to obtain the measurement data instead of detecting phase relationships of received microwave signals.

Other and still further object, features and advantages of the present invention will become apparent upon a reading of the following detailed description of a preferred form of the invention.

SUMMARY OF THE INVENTION

By the use of microwaves it is possible to determine the thickness of a dielectric coating, such as paint, or automotive body fillers used for packing dents, applied to either a metallic or a highly conductive composite base such as one comprising graphite. In regard to the later, bases such as graphite composites possess electrical conductivity similar to that of many metals when exposed to microwave frequencies. Where the number of discrete layers of paint and their combined thickness are reasonably known from the original manufacturer's specifications, the detection of abnormally thick dielectric substances on a vehicle body probably indicates the presence of paint layers added after the manufacture of the product or the presence of a body filler material, either or both of which would suggest prior damage and subsequent repair.

The process of the present invention is accomplished by the novel modification of a basic microwave transmitting and receiving apparatus such as would be found in a traditional door opener module, including the oscillator, waveguide, and detector diode. This module operates at a factory preset frequency with a detector located at a fixed location with respect to the waveguide aperture. The use of such off-the-shelf components decreases the cost of the final coating layer counter product. The modifications to the existing motion detector apparatus which make such a module usable to satisfy the objects of the present invention are significant elements of the invention, which will be described.

In the microwave module, a transmitted signal having one direction and the received reflected signal having an opposite direction become superimposed on one another inside the waveguide, setting up a wave disturbance which is not progressive, that is, a standing wave. A diode type of detector is provided at a fixed location in the waveguide to measure the disturbance, or voltage, of the standing wave at the location of the detector. Ordinarily, for an application such as the one to be described herein, the precise location of the detector within the waveguide would be an important parameter in making the required measurements. However, by using an off-the-shelf microwave unit certain adjustments and compensations must be made in order to accommodate the requirements of the counter, vis-à-vis the predetermined location of the detector. In order to adapt the fixed detector location of the microwave unit to the particular needs of this invention, an electrically lossy dielectric layer, such as carbonized rubber, is layered onto a rigid flange which is perpendicularly attached to the distal end, or aperture, of the waveguide. The lossy layer attenuates and shapes the wave form, thereby electrically-adjusting the electrical location of the detector diode. The lossy layer also acts to stabilize the microwave output signal so that measurement repeatability is significantly increased over similarly proposed devices of the prior art. Upon measuring the standing wave voltage, the output of the diode detector is amplified and fed to an electrical comparator whose output energizes one or more light emitting diodes (LEDs) which indicate one or more coating layers respectively.

THE DRAWINGS

DETAILED DESCRIPTION

Figure 1:
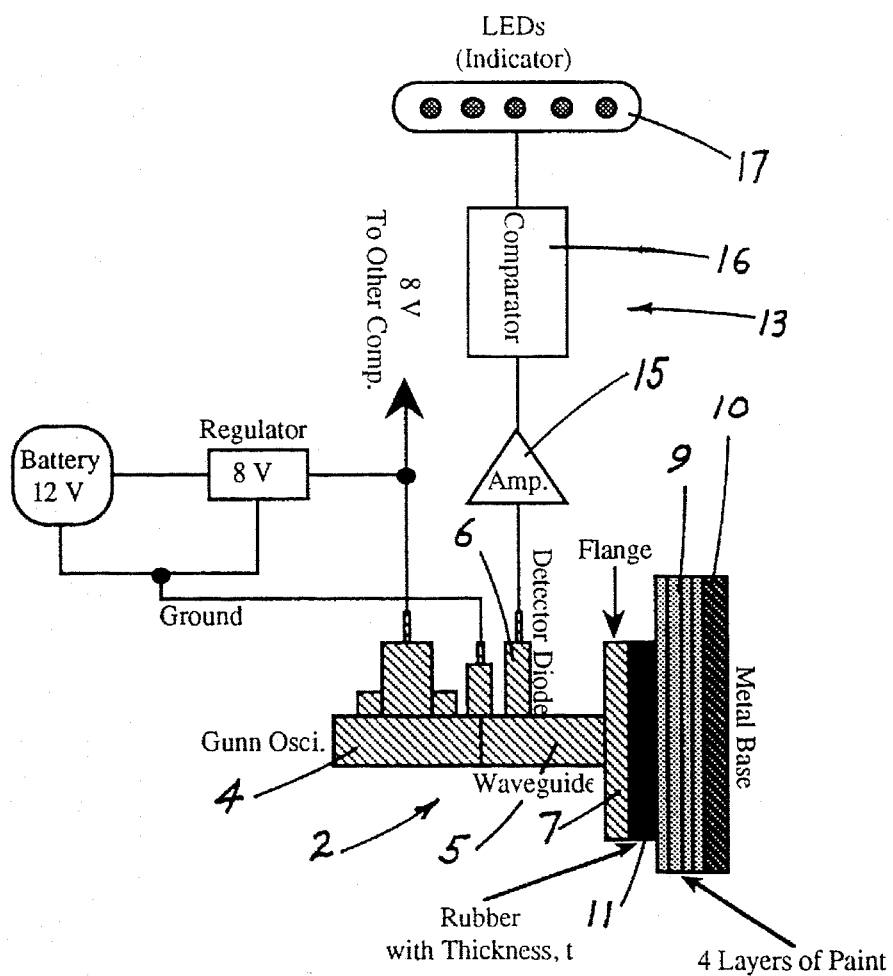
FIG. 1 is a diagrammatic schematic of the circuity and essential physical apparatus of the apparatus of the present invention.

Referring first to FIG. 1 of the drawings, a microwave transmitting module is indicated generally by the reference numeral 2. The module comprises a Gunn oscillator 4, a waveguide 5 and a diode detector 6 which are integrated together as one small transmitter and receiver operating at a typical frequency in the 10 to 30 GHz range. A supply voltage of 8 volts excites the Gunn oscillator which produces a microwave signal whose frequency becomes set by the cavity resonator in which the Gunn oscillator is housed. The microwave signal travels through the waveguide 5 and exits the waveguide via its aperture, becoming the incident wave which illuminates a target, such as the paint layers 9 on top of a metal base 10. Upon reflection of the electromagnetic microwave from the target 9 and 10, the wave reenters the aperture of the waveguide, becoming superimposed upon the transmitted incident wave, producing a standing wave within the waveguide 5. The diode detector 6 measures the standing wave voltage at the diode location and produces a DC output voltage which is a function of a variable and several constants which are built into the apparatus. The measured standing wave voltage is a function of the magnitude and frequency of the incident wave, both of which are fixed for the particular apparatus and are therefor constant. The voltage measured is also a function of the magnitude of the reflected signal which is dependent on the characteristics of the target being scrutinized, such as the thickness of the paint on the target and the paint's dielectric properties, which in turn may depend on the quality of the paint. Because the voltage of the standing wave varies along its length within the waveguide, the location within the waveguide of the diode detector also influences the measurement, however the detector is in a fixed location in the microwave module being described and therefor the location element also becomes a constant. Considering then that all of the elements which can effect the voltage measurement are constant except the magnitude of the reflected microwave signal, it is seen that the thickness of the paint coating can be directly related to the magnitude of the reflected signal and hence to the magnitude of the standing wave voltage measurement.

Figure 2:
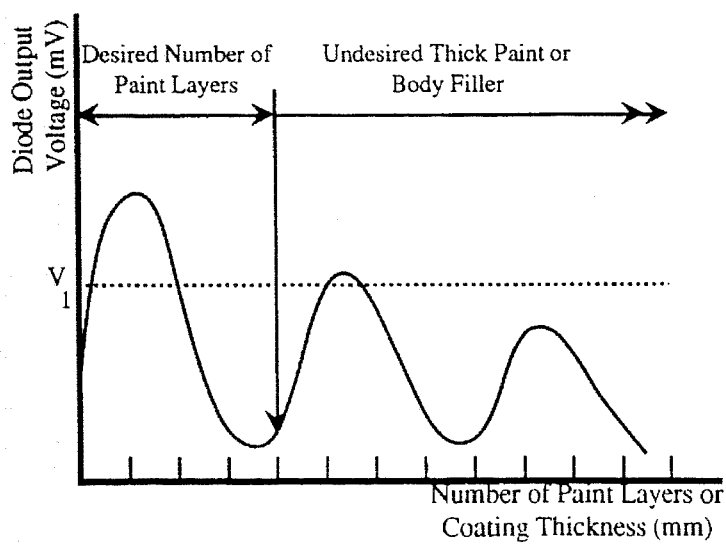
FIG. 2 illustrates a typical detector diode voltage output characteristic in a standard off-the-shelf microwave module, plotted against a number of paint or coating layers which might typically be detected when using such a module in an modified condition in a device for accomplishing the method of the present invention.
Figure 3:
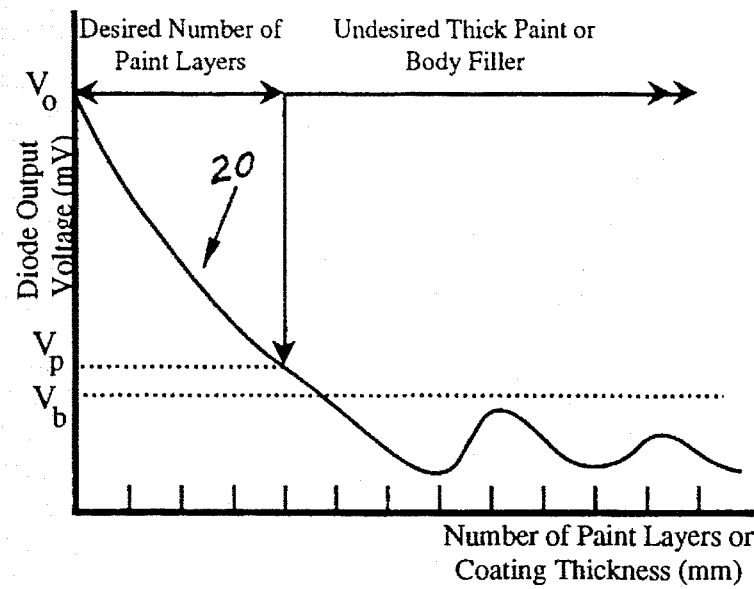
FIG. 3 shows, in larger scale that FIG. 2, the approximately linear region of the standing wave which results from passing the electromagnetic wave through a loss producing material. The linear portion of the wave is the portion over which it is desirable to take the diode detector measurements.

The location of the detector diode 6 in the waveguide 5 in the module 2, designed for use as a component in a door opening device or other type of motion sensor, is not ideally suited for the purposes intended by the present invention. As will be seen from an examination of FIG. 2, the measured voltage $V_1$ cannot be relied upon in an off the shelf waveguide module configuration (such as the door opener type previously referred to) to provide reliable information about the number of paint layers because that single voltage measurement presents an ambiguity as to whether there is one-half of a layer, two, five or six layers. Therefore, in order to detect a discrete voltage which represents a single value of coating thickness or a distinct number of coating layers, the standing wave voltage must be measured at a point along a linear portion of its wave form. However, to make the measurement in the linear region of the wave form it is necessary to electrically "reposition" the detector diode. This electrical repositioning is accomplished by adding a layer of material to the outer flange of the waveguide so that the layer is positioned normally to the direction of the waveguide radiation. The material comprising the layer may be any substance which will attenuate or create power loss ("lossy") in the incident and reflected electromagnetic waves passing through it, such as, for example, carbonized rubber. In the preferred form of the invention the layer of material comprises a rubber pad 11 having approximately 30% carbon content. The rubber sheet 11 is positioned over the outer surface of a rectangularly shaped waveguide flange 7 having a central opening congruent with the opening of the waveguide 5. The thickness (t) of the pad 11 is appropriate to correctly space the metallic base 10 of the tested target at such a distance from the detector diode that the standing wave present in the waveguide will present its most linear portion to the position occupied by the detector diode 6. The dielectric properties and the thickness of the carbonized rubber pad 11 act together to provide several beneficial advantages. The first function of the rubber sheet is to electrically reposition the diode detector 6 so as to accommodate the requirements of the apparatus of the present invention, as previously described. This is accomplished in two ways. First, by the choice of materials for the "lossy" layer to properly manage the action of the sheet as an absorber or attenuator of part of the microwave energy of the transmitted and reflected waves. Second, by regulating the spacing dimension provided by the thickness of the pad 11. By judicious selection of these two factors it is possible to locate the point of taking of the diode output voltage measurement within the linear portion 20 (See FIG. 3) of the standing wave voltage characteristic so that the undesired measurement ambiguity, as shown in FIG. 2, disappears in the desired range of paint layers to be counted. FIG. 3 shows, by reference numeral 20, the approximately linear region of the standing wave shape where the diode detector measurements are taken as a result of the use of a properly dimensioned "lossy" layer, comprising the carbonized rubber sheet 11 covering the aperture of the waveguide 5. In the preferred form of invention, using an off the shelf microwave generator and waveguide and the approximately 30% carbonized rubber as the layer material, the spacing dimension, or thickness (t) of the layer 11, is ¼ inch. Referring to FIG. 3, $V_o$ indicates the measured voltage for a situation where there is no paint or dielectric coating on the metal base 10. $V_p$ indicates the measured voltage for the desired maximum number of paint layers or the coating thickness that the particular embodiment of the invention would be designed to count or measure. $V_b$ indicates the voltage at which an undesired number of paint layers or a body filler is detected. An undesired number of layers is some number of layers which is of no interest to count, such as more than four, for example. Because of the diode detector's position, vis-a-vis the paint layers on the tested surface, the linear portion 20 of the standing wave voltage curve becomes equivalent to the desired range of coating or filler thickness. Furthermore, the voltage level at which a body filler material is detected is now less than the voltage for any other number of paint layers, thus eliminating any measurement ambiguity. For instance, it is not required or desirable to try to measure more than three or four layers of paint, since more than one layer would be an indication of the vehicle having been repainted with the old paint not having been removed.

Figure 4:
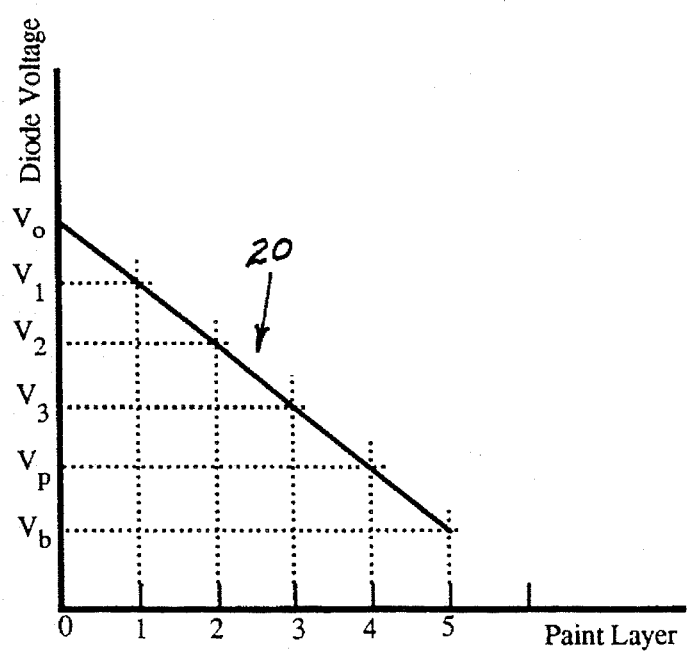
FIG. 4 is a diagrammatic graph illustrating the relationship between voltage measurements over the linear portion of the standing wave and the numbers of paint layers corresponding to the various voltage measurements.
Figure 5:
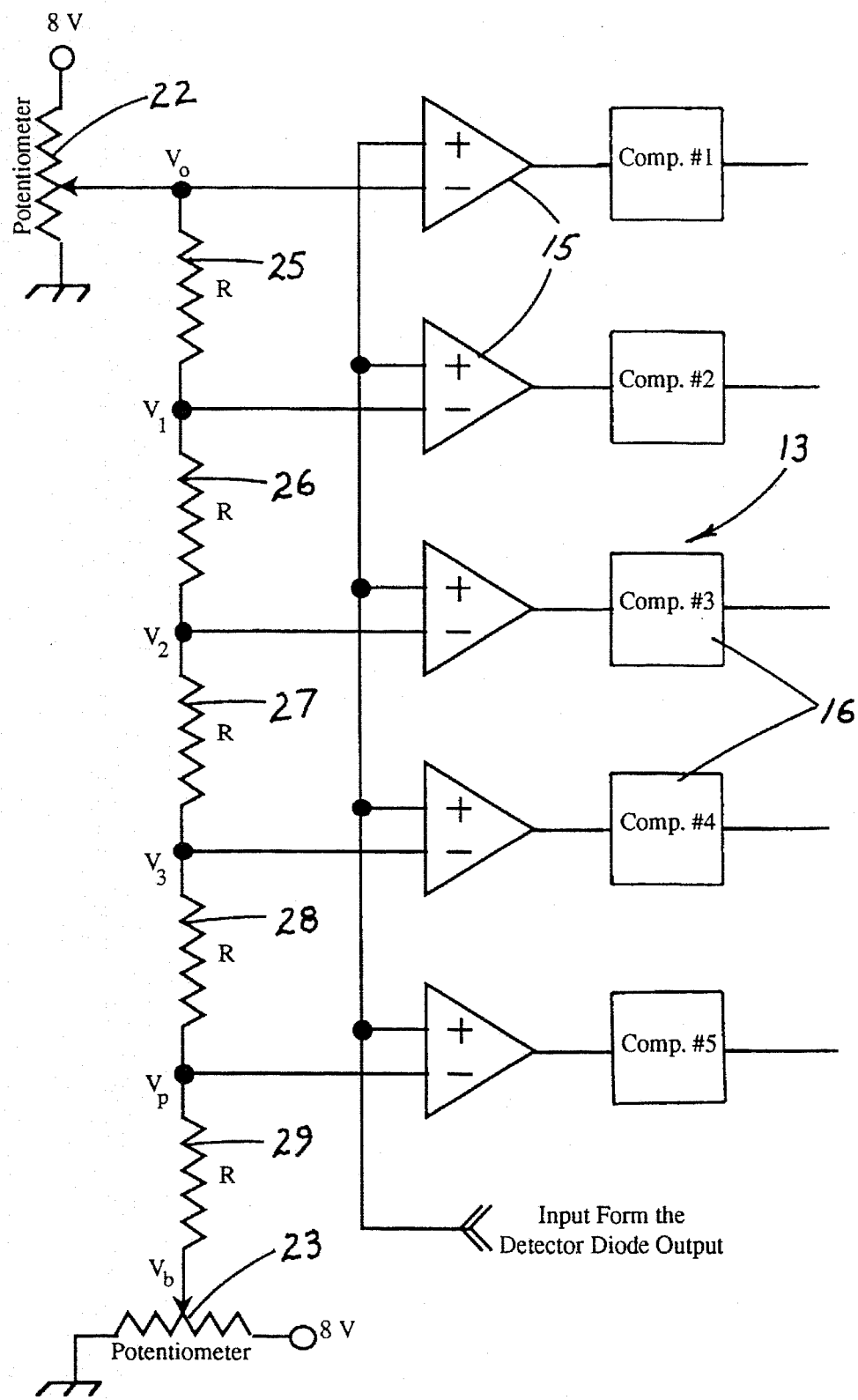
FIG. 5 is a typical circuit diagram of a number of voltage comparators and the calibrating voltage divider which presets the comparators.

The voltage range between $V_o$ and $V_p$, which is not ambiguous, is now used to determine the number of paint layers 9, or coating thickness, which has been applied to a metallic or highly conductive base 10. As seen in FIGS. 3 and 4, this voltage variation is approximately linear through a suitably large range so that the voltage spread in this range can be subdivided and made equivalent to a selected number of paint layers 9. In the preferred form of the invention the voltage $V_p$ indicates four layers of paint. A voltage less than $V_p$ would indicate very thick paint or the presence of body filler material, both of which would be probable cause for concern. Thus, the voltage range between $V_o$ and $V_p$ may be used, in conjunction with either analog or digital interpretive circuitry to indicate, to the user of the instrument, the number of paint layers or coating thickness existing on the conductive base material, such as the metal body of a vehicle.

The voltage represented by the linear portion of the curve of FIG. 3 is transmitted to an analog comparator system 13 in which a plurality of amplifiers 15 and comparators 16 produce to an indicator 17 an output representing one, two, three, four and more than four layers of paint. The comparators 16 are pre-programmed with information relative to the typical thickness of paint layers. By comparing the standing wave voltage, as measured by the detector diode 6 and representing coating thickness, with the known typical thickness of paint layers, the comparator is able to derive an output which is indicative of the number of layers of a coating on the metallic surface or to indicate that the metal surface is far beyond the distance of even a plurality of paint layers, indicating the presence of a body filler which has been employed to fill or smooth out a depression in the metallic surface of the target. The output of each comparator is directed to a display device 17, which may preferably be a series of light emitting diodes (LED's) which are responsive to the output signals of each respective one of the comparators. The voltage range between $V_o$ and $V_p$ is preferably divided into four voltages, each corresponding to a distinct number of paint layers, as shown in FIG. 4. The comparator input reference voltages are then set so that any measured voltage whose amplitude is between $V_o$ and $V_1$ turns on the first LED. Voltage amplitude between $V_1$ and $V_2$ turns on the second LED. Voltage between $V_2$ and $V_3$ turns on the third LED and that between $V_3$ and $V_4$ rams on the fourth LED. A voltage amplitude of less than $V_p$ turns on the fifth LED, warning of the detection of the maximized number of paint layers or coating thickness.

As briefly stated above with respect to programming the comparators for known thicknesses of paint layers, it is necessary within that process to set the reference voltages so that certain voltage levels will correspond to selected numbers of coating layers. However, since the detector diode 6 is sensitive to static charges, any spark or electrical surge from activating an off/on switch or using a battery charger may cause a total upward or downward shift in the diode voltage characteristics which are depicted in FIG. 4. Therefore, if the comparator reference voltages illustrated in FIG. 4 are hard set, such upward or downward shifts will result in erroneous indications of the number of coating layers. To alleviate this problem, two potentiometers 22 and 23 are used to calibrate the $V_o$ and $V_p$ voltage values which are used as the comparator references. The calibration is done by the use of two known calibration targets. One target comprises a metal base without paint. A second calibration target comprises a metal base having four layers of paint. By activating the microwave unit and directing the incident waves to the two calibrating targets in sequence, the values of $V_o$ and $V_p$ may be adjusted by the potentiometers 22 and 23 to indicate zero paint layers for $V_o$ and four paint layers for voltage $V_p$. Intermediate voltage values for one, two and three layers of paint are then automatically set by the resistors 25, 26, 27, 28 and 29 which form a five part equal voltage divider across the inputs to the comparator amplifiers 15.

The potentiometers 22 and 23 are also useful in calibrating the apparatus to accommodate different grades of paint, it being seen that paint quality and its dielectric properties may function to slightly vary the voltage range $V_o$–$V_p$. Likewise, if a sophisticated user were to know that the thickness of the paint layers on a specific target were supposed to be somewhat different than the thickness programmed into the comparators, such thickness difference could also be accommodated by adjustment of the calibrating potentiometers, thus permitting customized use of the device.

While electrical comparators comprise the preferred form of the invention, other alternative devices may be employed. A digital microcontroller may be used, for example. In this alternative embodiment of the invention the desired voltage settings $V_o$ and $V_p$ are, prior to each use, fed to the microcontroller via a simple momentary switch which replaces the two calibrating potentiometers in the preferred form of the invention. For this alternative embodiment the calibrating targets comprise a non-coated metal sheet and a metal sheet with a 0.1 mm coating. Use of these two targets establishes as references the voltages $V_o$ and $V_1$. Since the diode output voltage changes quite linearly in the range of coating thicknesses, then to deduce the thickness of an unknown sample, its measured voltage will be compared with the two reference voltages and the difference between $V_1$ and $V_o$ will be equal to the voltage difference per every 0.1 mm of thickness change. For example, if the measured diode output voltage for an unknown coating is $\{V_o - N(V_1 - V_o)\}$, then the thickness of this coating is N times 0.1 mm. A non-integer value of N will be approximated by using the nearest lower integer to N. For example, a voltage measured to be 4.5 times that of the 0.1 mm thickness voltage will indicate a thickness of 4 times 0.1 mm, or 0.4 mm.

In the event that the coating thicknesses are greater than a few millimeters, the device may be constructed so as to operate at a lower microwave frequency and the objects of the invention will thereby be satisfactorily achieved. Although the preferred form of the invention has been described in terms of an off the shelf microwave product and the modifications necessary to implement its use for the purpose of the present invention, it is not the intent of the inventors to thereby limit the scope of the invention. A device in accordance with the teachings of the invention could easily be designed and made solely to satisfy the purposes of the present invention.

We claim:

1. Apparatus for the nondestructive evaluation of the character of target defining dielectric coatings which have been applied to an electrically conductive base material, including;

a microwave transmitter and receiver, comprising, waveguide means having an interior and a communicating aperture for propagating incident electromagnetic radiation in the microwave frequency range and for receiving through said aperture a reflected wave thereof to establish a standing wave within the interior of the waveguide means, a microwave oscillator having an output directed into the interior of the waveguide means, microwave voltage detector means having an output and disposed within the interior of the waveguide for measuring the voltage of the standing wave over a substantially linear portion of the standing wave therein, and the improvement comprising, a layer of lossy material disposed over the aperture of the waveguide means and adapted to abut the target, the thickness of said material providing a fixed distance between the aperture and the surface of the target, a plurality of comparator means receiving the output of the voltage detector means and having individual outputs which are each a function of the similarity between the voltage received from the voltage detector means and a pre-selected voltage range programmed into each of the comparator means, and a like plurality of display means, each responsive to the output of a respective one of the comparator means for indicating the layer characteristics of the dielectric coating on the electrically conductive base material of the target.

2. The apparatus of claim 1 wherein the flat layer of material comprises microwave energy absorbing means.

3. The apparatus of claim 1 where the means indicating the presence of an output of each comparator includes a light emitting diode connected to the output of each comparator.

4. The apparatus of claim 1 and further including source means of a like plurality of different voltages applied respectively to the individual comparator means for supplying the pre-selected voltage range programmed into each of the comparator means.

5. The combination of claim 4 and further including calibration means connected to the source means for calibrating the comparator means.

6. A method for determining the number of layers of a dielectric coating applied to an electrically conductive base material, including the steps of, generating electromagnetic waves having a microwave frequency, propagating the waves perpendicularly to the base material, receiving the waves which are reflected from the base material so that such reflected waves are superimposed upon the propagated waves to form a standing wave, detecting the voltage of the standing wave within a linear region of the wave, comparing the detected standing wave voltage with a predetermined set of voltage values, and displaying an indication of the thickness of the dielectric coating as a function of the relationship between the detected standing wave voltage and at least one of the predetermined set of voltage values.

7. The method of claim 6 where the display includes one of a plurality of possible indications which one indication is a function of the relationship between the detected standing wave voltage and one voltage of the predetermined set of voltages which one voltage is representative of a pre-established number of coating layers.

* * * * *